(12) United States Patent
Rakitzis

(10) Patent No.: US 9,903,805 B2
(45) Date of Patent: Feb. 27, 2018

(54) CAVITY ENHANCED POLARIMETER AND RELATED METHODS

(71) Applicant: Theodore Peter Rakitzis, Heraklion-Crete (GR)

(72) Inventor: Theodore Peter Rakitzis, Heraklion-Crete (GR)

(*) Notice: Subject to any disclaimer, the term of this patent is extended or adjusted under 35 U.S.C. 154(b) by 0 days.

(21) Appl. No.: 15/647,106

(22) Filed: Jul. 11, 2017

(65) Prior Publication Data

US 2017/0315050 A1    Nov. 2, 2017

Related U.S. Application Data

(63) Continuation-in-part of application No. 14/706,743, filed on May 7, 2015, now Pat. No. 9,702,812.

(Continued)

(51) Int. Cl.
*G01N 21/19* (2006.01)
*G01J 4/04* (2006.01)
(Continued)

(52) U.S. Cl.
CPC .............. *G01N 21/19* (2013.01); *G01J 4/02* (2013.01); *G01J 4/04* (2013.01); *G01N 21/21* (2013.01);
(Continued)

(58) Field of Classification Search
CPC ...... G01N 21/19; G01N 21/21; G01N 21/211; G01N 21/23; G01N 2201/06113;
(Continued)

(56) References Cited

U.S. PATENT DOCUMENTS

| | | |
|---|---|---|
| 5,437,840 A | 8/1995 | King et al. ................. 422/82.08 |
| 5,538,850 A | 7/1996 | King et al. .................. 435/6.12 |

(Continued)

OTHER PUBLICATIONS

Bougas, Lykourgos et al., "Chiral cavity ring down polarimetry: Chirality and magnetometry measurements using signal reversals," 2015, The Journal of Chemical Physics, 143, pp. 104202-1 to 104202-8.*

(Continued)

*Primary Examiner* — Gordon J Stock, Jr.
(74) *Attorney, Agent, or Firm* — Booth Udall Fuller, PLC

(57) ABSTRACT

A polarimeter for measuring chirality of a material comprising an optical ring cavity comprising a plurality of reflective elements configured to promote bi-directional propagation of a laser beam within the cavity, a laser-emitting device configured to introduce a first input beam and a second input beam into the cavity, a Faraday rotator, a phase compensator, an acousto-optic modulator configured to shift the frequency of the first output beam, an optical recombination device configured to recombine shifted and unshifted output beams, and first and second detectors configured to receive the recombined beams, wherein the plurality of reflective elements, Faraday rotator, and phase compensator are configured such that light from the first and second input beams passes through a chiral material located within the cavity a sufficient number of times for a measurement of optical rotary dispersion and circular dichroism of light transmitted through the material to be obtained at the detectors.

20 Claims, 14 Drawing Sheets

Related U.S. Application Data

(60) Provisional application No. 61/990,634, filed on May 8, 2014.

(51) Int. Cl.
    *G01J 4/02* (2006.01)
    *G01N 21/21* (2006.01)
    *G01J 4/00* (2006.01)

(52) U.S. Cl.
    CPC .. *G01J 2004/001* (2013.01); *G01N 2201/067* (2013.01); *G01N 2201/0636* (2013.01); *G01N 2201/06113* (2013.01)

(58) Field of Classification Search
    CPC ..... G01N 2201/0636; G01N 2201/067; G01N 2201/066; G01N 2201/0668; G01N 2201/068; G01N 2201/0683; G01N 2201/0692; G01N 2021/212; G01N 2021/213; G01N 2021/216; G01N 2021/217; G01N 2021/218; G01J 4/00; G01J 4/02; G01J 4/04; G01J 2004/001; G01J 2004/002; G01J 2004/004; G01J 2004/005; G01J 2004/007; G01J 2004/008
    USPC .................................................. 356/364–370
    See application file for complete search history.

(56) References Cited

U.S. PATENT DOCUMENTS

| | | | |
|---|---|---|---|
| 5,835,231 A | 11/1998 | Pipino | 356/440 |
| 5,943,136 A | 8/1999 | Pipino et al. | 356/440 |
| 5,986,768 A | 11/1999 | Pipino | 356/440 |
| 6,034,770 A * | 3/2000 | Kim | G01C 19/66 356/459 |
| 6,466,322 B1 * | 10/2002 | Paldus | G01N 21/39 356/437 |
| 6,483,858 B1 * | 11/2002 | Hovater | H01S 3/10092 372/18 |
| 6,515,749 B2 | 2/2003 | Pipino | 356/440 |
| 7,054,009 B2 | 5/2006 | DePue et al. | 356/437 |
| 7,301,639 B1 | 11/2007 | Kebabian et al. | 356/437 |
| 7,333,206 B2 | 2/2008 | Clark | 356/446 |
| 7,336,359 B1 | 2/2008 | Simpson et al. | 356/364 |
| 9,702,812 B2 * | 7/2017 | Rakitzis | G01J 4/02 |
| 2005/0094150 A1 | 5/2005 | DePue et al. | 356/445 |
| 2005/0225775 A1 | 10/2005 | Brunfeld et al. | 356/519 |

OTHER PUBLICATIONS

Silverman, M.P. et al, Large Enhancement of Chiral Asymmetry in Light Reflection Near Critical Angle. Optics Communication vol. 74, No. 3, 4. 1989.

Lenker, John, Optical Properties of Isotropic Chiral Media. 1994.

Porison, Jeromoe et al., Resonant Cavity Gas-Phase Polarimeter. Technical Notes,1998.

Muller, Thomas et al., Cavity Ring-Down Polarimetry (CRDP): A new scheme for probing circular birefringence and circular dichroism in the gas phase. 2000.

Hall, John L et al., Measurement of mirror birefringence at the sub-ppm level: proposed application to a test of QED. 2000.

Baily, Giles et al., Highly sensitive frequency metrology for optical anisotropy measurements. 2010.

Baev, V.M., Laser intracavity absorption spectroscopy, 1999.

Wolf Von Klitzilng, Frequency tuning of the whispering-gallery modes of silica microspheres for cavity quantum electrodynamics and spectroscopy, 2000.

Dimitris Sofikitis, Evanescentwave and ambient chiral sensing by signal-reversing cavity ringdown polarimetry, 2014.

* cited by examiner

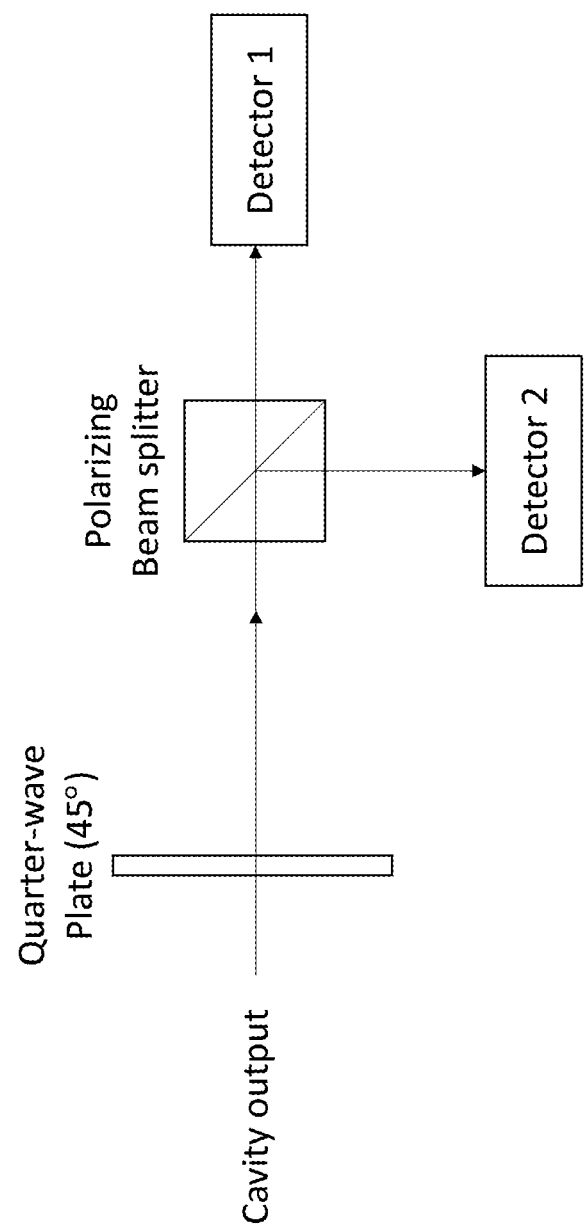
FIG. 12 – PRIOR ART

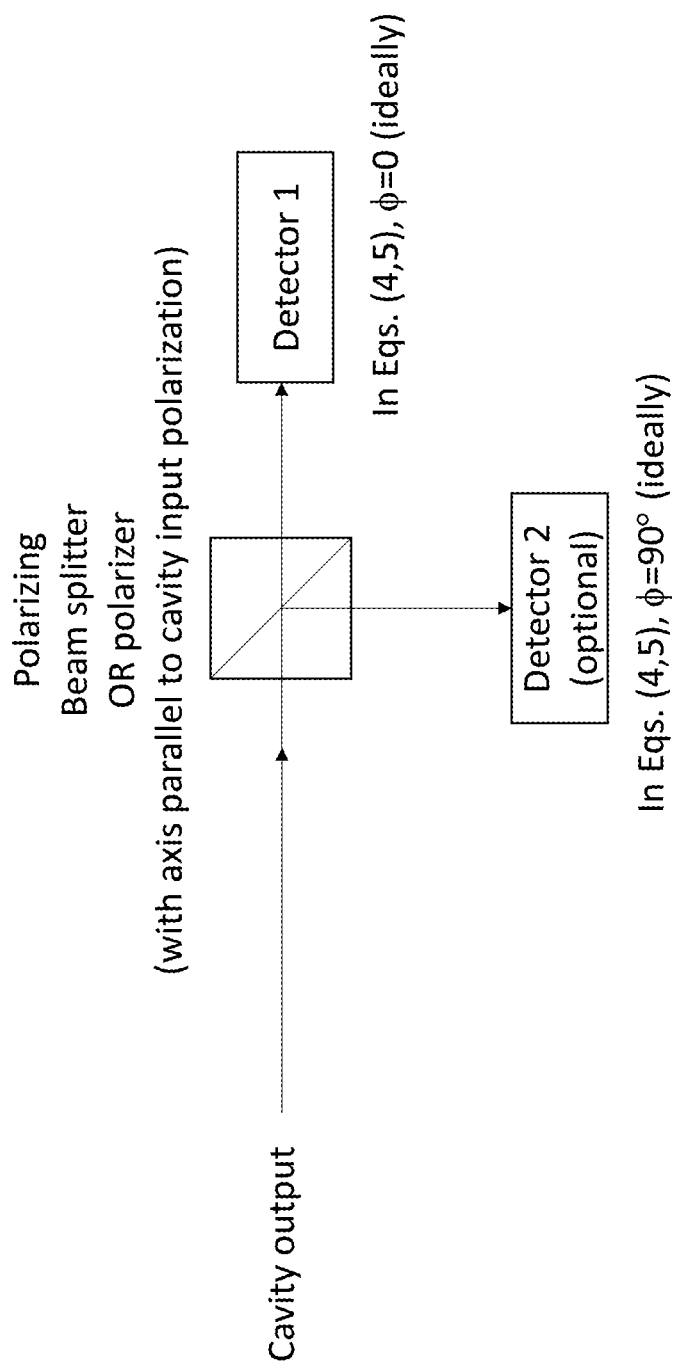
FIG. 13 – PRIOR ART

CAVITY ENHANCED POLARIMETER AND RELATED METHODS

CROSS REFERENCE TO RELATED APPLICATIONS

This document is a continuation in part of earlier U.S. patent application Ser. No. 14/706,743, entitled "Cavity Enhanced Polarimeter and Related Methods" to T. Peter Rakitzis, which was filed May 7, 2015, now pending, which claims the benefit of the filing date of U.S. Provisional Patent Application No. 61/990,634, entitled "Cavity Enhanced Polarimeter" to T. Peter Rakitzis, which was filed on May 8, 2014, the disclosures of each of which are hereby incorporated by this reference.

BACKGROUND

1. Technical Field

This disclosure relates to a polarimeter. In particular, the polarimeter may be used to measure the chirality of molecular samples through the measurement of the optical rotation of plane polarized light or circular dichroism.

2. Background Art

Detecting and measuring chirality has applications in a diverse array of fields such as the pharmaceutical, cosmetics, and food industries as well as the more general fields of medicinal and biological chemistry, chemical synthesis and analysis of microsamples, proteomics, and ecology, surface catalysis, nucleation, and cell membrane reactions, to name a few.

Conventional polarimeters, which measure an angle of rotation caused by passing polarized light through an optically active material, work by passing light through a material sample and using typical configurations, the light makes only a single pass through the sample. While useful for the typical purposes of polarimeters, the structure which permits the single pass of light through the sample also limits the potential usefulness of the polarimeter.

Gas-phase chirality measurements, using a bowtie cavity and continuous-wave (cw) lasers and measurement, are described in the article by L. Bougas, et al., *Cavity-Enhanced Parity-Nonconserving Optical Rotation in Metastable Xe and Hg*, Physical Review Letters, 25 May 2012, vol. 108, 210801 (2012), the disclosure of which is incorporated herein by reference. The gas-phase measurements, however, do not address how to accomplish liquid-phase and interfacial determination of chirality, or how to measure chirality using a pulsed laser The measurement of chirality of materials is most commonly measured optically using circular dichroism (CD), the preferential absorption of right compared to left circularly polarized light, or optical rotatory dispersion (ORD), the rotation of the plane of linearly polarized light as it is transmitted through a sample. Experimental signals from both CD and ORD are usually very small. For example, the CD asymmetry parameter g is typically of order $10^{-4}$, so that nearly optically thick chiral samples demonstrate differences in absorption between right and left circularly polarized light of order $10^{-4}$. The ORD angle is proportional to optical pathlength and the sample concentration. Typically, commercial polarimeters for ORD measurements use cells with pathlengths of 1-10 cm, so that the ORD angle can be large enough to be measured accurately which require a large sample sizes most likely on the order of many milliliters of a substance. The optical principles behind measuring CD and ORD have remained largely unchanged for many decades.

The measurement of CD or ORD in an evanescent wave at the total internal reflection (TIR) of a light beam at the surface of a prism can give experimental signals of order g (i.e. CD signal differences of about $10^{-4}$, or ORD angles of about $10^{-4}$ rad), where g is the chiral asymmetry in the refractive index of right and left circularly polarized light given by $n_\pm = n \pm g$ (where $n_+$ and $n_-$ are the refractive indices of a chiral medium for right and left circularly polarized light, respectively). Silverman and Lekner showed that close to the TIR critical angle, the chiral signals are enhanced. This is shown by the following equation (derived following the treatment of Lekner) for the optical rotation angle $\Theta_{EW}$ following TIR, from the placement of a chiral sample in the evanescent wave of the prism:

$$\Theta_{EW} \cong \frac{\Delta n}{n} \frac{N}{1-N^2} \frac{\cos\theta}{\sqrt{\sin^2\theta - N^2}} \quad (1)$$

where $\theta$ is the incidence angle, $\Delta n = (n_+ - n_-)$, $n = (n_+ + n_-)/2$, $n_+$ and $n_-$ are the refractive indices of the chiral sample for left and right circularly polarized light, respectively, $N = (n/n_p)$, and $n_p$ is the refractive index of the prism. The $\Theta_{EW}$ increases sharply near critical angle ($\sin\theta \approx N$), and also near index matching ($N \approx 1$).

In the last 15 years, Poirson and Vaccaro pioneered the use of optical cavities to increase the path length to measure ORD of chiral vapors, by introducing two quarter wave plates in and at either ends of a two-mirror cavity. The pair of quarter wave plates carries out two functions: 1) for each pass, the light polarization is reflected through the optical axis of the wave plate so that the optical rotation of the forward and backward light path sums instead of cancelling, and 2) the optical axes of the two waveplates are offset by angle $\alpha$, so that the light polarization is rotated by $2\alpha$ for each roundtrip pass. Vaccaro showed that if $2\alpha \gg \eta$ (where $\eta$ is the linear birefringence in the cavity, which normally causes great problems in measuring the small optical rotation of the sample), then the negative effects of the linear birefringence become negligible. However, this cavity-based technique has only been applied to vapor samples. The main problem of these linear cavities is that the signal of the chiral sample needs to be compared to the signal of a null sample. As it is difficult to alternate reproducibly between the sample and the null, and significant time is needed to do so (typically many seconds), the background subtraction of the null signal does not typically allow the measurement of small signals (e.g. smaller than about 0.1 mdeg/pass).

Very recently, Bougas et al. described a bowtie cavity with counter-propagating laser beams and an intercavity magneto-optical crystal using an applied longitudinal magnetic field. This crystal caused an optical rotation of the polarization with the same advantages as that caused by the quarter wave plates described above. However, in addition, Bougas et al. showed that the sample optical rotation angle can be reversed in sign by inverting the sign of the magnetic field. This gives an experimental control for isolating small experimental signals, without needing to remove the sample and replace with a null sample. This magnetic field reversal can be used as an efficient and rapid subtraction procedure to isolate the small chiral signal from much larger backgrounds. Bougas et al. described an experimental setup that allowed measurements using continuous wave (cw) lasers and measurement methods, on low-loss gas-phase samples.

To reduce the length and complexity of the detailed description and to establish a current state of the art, Applicant hereby incorporates by reference in their entirety each reference listed in the numbered paragraphs below:

M. P. Silverman, J. Badoz, "Large enhancement of chiral asymmetry in light reflection near critical angle" Optics communications 74, 129 (1989).
J. Lekner, "Optical properties of isotropic chiral media" Pure Appl. Opt. 5, 417 (1996).
J. Poirson, M. Vallet, F. Bretenaker, A. L. Floch, and J. Thepot, Anal. Chem. 70, 4636 (1998).
T. Müller, K. B. Wiberg, P. H. Vaccaro, J. Phys. Chem. A, 104, 5959 (2000).
J. L. Hall, J. Ye, and L.-S. Ma, Phys. Rev. A 62, 013815 (2000).
G. Bailly, R. Thon, and C. Robilliard, Rev. Sci. Instrum. 81, 033105 (2010).
V. M. Baev, T. Latz, P. E. Toschek, Appl. Phys. B 69, 171-202 (1999).
W. von Klitzing, R. Long, V. S. Ilchenko, J. Hare, V. Lefevre-Seguin, Optics Letters 26, 166-8 (2001).

SUMMARY

According to one aspect, a polarimeter for measuring chirality of a material includes an optical ring cavity comprising a plurality of reflective elements configured to promote bi-directional propagation of a laser beam within the cavity, and a laser-emitting device configured to introduce a first input laser beam and a second input laser beam into the ring cavity. The polarimeter further includes a Faraday rotator and a phase compensator, the Faraday rotator and the phase compensator configured to suppress a birefringent background as the first and second laser beams pass through the ring cavity, and an acousto-optic modulator configured to receive a first output laser beam from the optical ring cavity, shift the frequency of the first output laser beam by an offset frequency, and produce a first shifted laser beam. Furthermore, the polarimeter includes an optical recombination device configured to receive the first output laser beam, a second output laser beam from the cavity, and at least the first shifted laser beam to produce a first combined laser beam and a second combined laser beam, and a first detector and a second detector. The first detector is configured to receive the first combined laser beam and the second detector is configured to receive the second combined laser beam.

The plurality of reflective elements, Faraday rotator, and phase compensator are configured such that light from the first and second input laser beams passes through a chiral material located within the ring cavity a sufficient number of times for a measurement of optical rotary dispersion (ORD) and circular dichroism (CD) of light transmitted through the chiral material and output as the first and second output laser beams to be obtained at the first and second detectors.

Particular embodiments may comprise one or more of the following features. The first combined laser beam may comprise the first shifted beam and the second output beam, and the second combined laser beam may comprise the first shifted beam and the first output beam. The acousto-optic modulator may be further configured to receive the second output laser beam from the ring cavity, shift the frequency of the second output laser beam by the offset frequency, and/or produce a second shifted laser beam. The optical recombination device may be further configured to receive the second shifted laser beam. The first combined laser beam may comprise the first shifted beam and the second output beam, and the second combined laser beam may comprise the second shifted beam and the first output beam. The polarimeter may further comprise a prism having at least a light input and light output surface comprising an anti-reflective coating such that light from the first and second laser beams is totally internally reflected for at least one surface of the prism at which the chiral material is located within an evanescent wave at the at least one surface of the prism. The polarimeter may further comprise a flow cell comprising one or more anti-reflective coated windows within which the chiral material is located. The light from the first and second laser beams may pass through the chiral material in a range of 100 to 10,000 times. A magnetic field of the Faraday rotator may be reversed such that the ORD signal is reversed, so that an absolute measurement of ORD of light passing through the chiral material is obtainable without requiring a null sample. The polarimeter may further comprise a whispering gallery mode microresonator (WGMM) configured to pass an electric current therethrough to produce a Faraday effect, such that a measurement of ORD and CD is obtained when the chiral material is located at a surface of the WGMM. The laser-emitting device may be configured to emit a continuous wave laser beam. The plurality of reflective elements may comprise four reflective elements and the optical ring cavity may comprise a bowtie ring cavity.

Implementations of a method of measuring chirality of a material includes promoting bi-directional propagation of a laser beam within an optical ring cavity of a polarimeter comprised of a plurality of reflective elements, introducing a first input laser beam and a second input laser beam into the ring cavity using a laser emitting device, suppressing a birefringent background as the first and second laser beams pass through the ring cavity using a Faraday rotator and a phase compensator, The method further includes shifting the frequency of the first output laser beam by an offset frequency using the acousto-optic modulator to produce a first shifted laser beam, combining the first output laser beam, a second output laser beam produced by the ring cavity, and at least the first shifted laser beam into a first combined laser beam and a second combined laser beam using an optical recombination device, and measuring the first combined beam using a first detector and the second combined beam using a second detector. The plurality of reflective elements, Faraday rotator, and phase compensator are configured such that light from the first and second input laser beams passes through a chiral material located within the ring cavity a sufficient number of times for a measurement of optical rotary dispersion (ORD) and circular dichroism (CD) of light transmitted through the chiral material and output as the first and second output laser beams to be obtained at the first and second detectors.

Particular aspects may comprise one or more of the following features. The method may further comprise receiving the second output laser beam at the acousto-optic modulator, and shifting the frequency of the second output laser beam by the offset frequency using the acousto-optic modulator to produce a second shifted laser beam. The second shifted beam may be combined with the first and second output beams and the first shifted beam using the optical recombination device to produce the first and second combined beams. The first combined laser beam may comprise the first shifted beam and the second output beam, and the second combined laser beam may comprise the second shifted beam and the first output beam. The method may further comprise totally internally reflecting light from the first and second laser beams for at least one surface of a prism having at least a light input and light output surface comprising an anti-reflective coating, the chiral material being located within an evanescent wave at the at least one surface of the prism for which the light is totally internally reflected. The method may further comprise obtaining an absolute measurement of ORD of light passing through the chiral material without requiring a null sample by reversing a magnetic field of the Faraday rotator. The method may also further comprise increasing a number of times the light from the first and second input laser beams passes through the chiral material using an intracavity gain medium within the cavity. The intracavity gain medium may amplify the light independent of a polarization state of the light. The laser-emitting device may emit a continuous wave laser beam.

Aspects and applications of the disclosure presented here are described below in the drawings and detailed description. Unless specifically noted, it is intended that the words and phrases in the specification and the claims be given their plain, ordinary, and accustomed meaning to those of ordinary skill in the applicable arts. The inventor is fully aware that he can be his own lexicographer if desired. The inventor expressly elects, as his own lexicographer, to use only the plain and ordinary meaning of terms in the specification and claims unless he clearly states otherwise and then further, expressly sets forth the "special" definition of that term and explains how it differs from the plain and ordinary meaning. Absent such clear statements of intent to apply a "special" definition, it is the inventor's intent and desire that the simple, plain and ordinary meaning to the terms be applied to the interpretation of the specification and claims.

The inventor is also aware of the normal precepts of English grammar. Thus, if a noun, term, or phrase is intended to be further characterized, specified, or narrowed in some way, then such noun, term, or phrase will expressly include additional adjectives, descriptive terms, or other modifiers in accordance with the normal precepts of English grammar. Absent the use of such adjectives, descriptive terms, or modifiers, it is the intent that such nouns, terms, or phrases be given their plain, and ordinary English meaning to those skilled in the applicable arts as set forth above.

Further, the inventor is fully informed of the standards and application of the special provisions of post-AIA 35 U.S.C. § 112(f). Thus, the use of the words "function," "means" or "step" in the Description, Drawings, or Claims is not intended to somehow indicate a desire to invoke the special provisions of post-AIA 35 U.S.C. § 112(f), to define the invention. To the contrary, if the provisions of post-AIA 35 U.S.C. § 112(f) are sought to be invoked to define the claimed disclosure, the claims will specifically and expressly state the exact phrases "means for" or "step for", and will also recite the word "function" (i.e., will state "means for performing the function of [insert function]"), without also reciting in such phrases any structure, material or act in support of the function. Thus, even when the claims recite a "means for performing the function of . . . " or "step for performing the function of . . . ," if the claims also recite any structure, material or acts in support of that means or step, or that perform the recited function, then it is the clear intention of the inventors not to invoke the provisions of post-AIA 35 U.S.C. § 112(f). Moreover, even if the provisions of post-AIA 35 U.S.C. § 112(f) are invoked to define the claimed disclosure, it is intended that the disclosure not be limited only to the specific structure, material or acts that are described in the preferred embodiments, but in addition, include any and all structures, materials or acts that perform the claimed function as described in alternative embodiments or forms of the invention, or that are well known present or later-developed, equivalent structures, material or acts for performing the claimed function.

The foregoing and other aspects, features, and advantages will be apparent to those artisans of ordinary skill in the art from the DESCRIPTION and DRAWINGS, and from the CLAIMS.

BRIEF DESCRIPTION OF THE DRAWINGS

Implementations will hereinafter be described in conjunction with the appended drawings, where like designations denote like elements, and:

FIG. 12 provides an exemplary diagram of detection of CD as known in the prior prior art.

FIG. 13 provides an exemplary diagram of detection of ORD as known in the prior art.

DESCRIPTION

Figure 1:
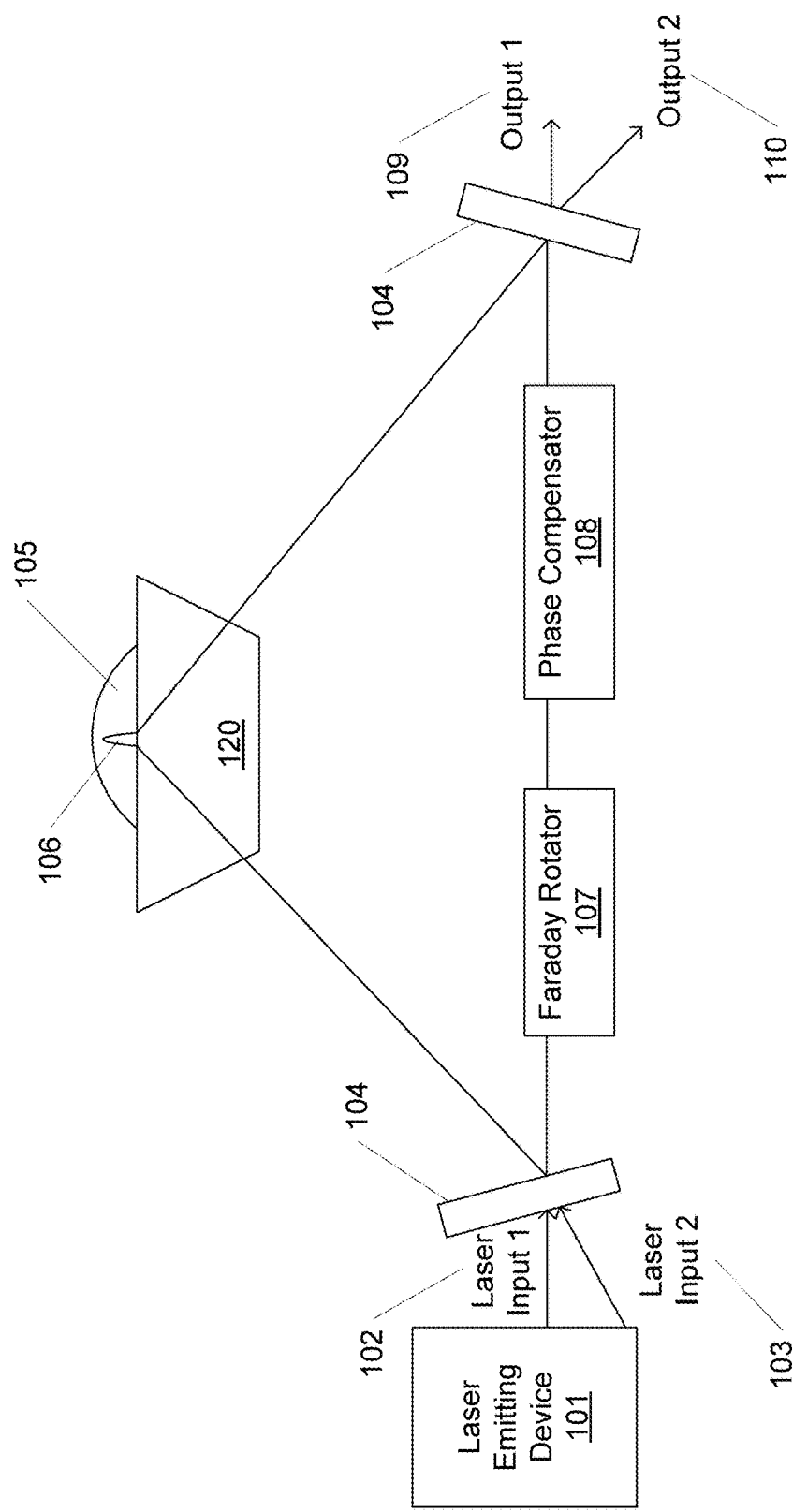
FIG. 1 is a block diagram of an exemplary configuration of a polarimeter comprising three reflective elements which introduces a chiral sample in an evanescent wave of a prism.

This disclosure, its aspects and implementations, are not limited to the specific polarimeters shown and described, or other system component examples, or methods disclosed herein. Many additional components, manufacturing and assembly procedures known in the art consistent with polarimeters are contemplated for use with particular implementations from this disclosure. Accordingly, for example, although particular implementations are disclosed, such implementations and implementing components may comprise any components, models, types, materials, versions, quantities, and/or the like as is known in the art for such systems and implementing components, consistent with the intended operation.

The word "exemplary," "example" or various forms thereof are used herein to mean serving as an example, instance, or illustration. Any aspect or design described herein as "exemplary" or as an "example" is not necessarily to be construed as preferred or advantageous over other aspects or designs. Furthermore, examples are provided solely for purposes of clarity and understanding and are not meant to limit or restrict the disclosed subject matter or relevant portions of this disclosure in any manner. It is to be appreciated that a myriad of additional or alternate examples of varying scope could have been presented, but have been omitted for purposes of brevity.

While this disclosure includes embodiments in many different forms, there is shown in the drawings and will herein be described in detail particular embodiments with the understanding that the present disclosure is to be considered as an exemplification of the principles of the disclosed methods and systems, and is not intended to limit the broad aspect of the disclosed concepts to the embodiments illustrated.

The following disclosure is directed to systems and methods relating to a polarimeter that utilizes cavity-enhancement techniques for the measurement of ORD and CD of chiral liquid and solid samples, both in bulk form and in the evanescent wave of prisms. These implementations allow the measurement of chirality of micro-volume and monolayer samples at the total internal reflection (TIR) surfaces of prisms. Such techniques may also be applied for measuring ORD and CD in chiral samples in a solution.

A ring optical cavity comprising at least three reflective elements allows bi-directional propagation of laser beams, which may be referred to as having clockwise (CW) and counter-clockwise (CCW) polarity. These two laser beams may be configured to enter and exit the cavity in different directions so that they can be controlled and probed separately. A magnetic field B may be applied to an intracavity magneto-optic window, such that a Faraday rotation $\theta_F$ is induced, with a sign determined by the sign of the B field. A chiral sample causes a rotation $\phi_C$. Subsequently, the cavity modes are split by frequencies $2\omega_{CW}$ and $2\omega_{CCW}$ (or, alternatively, linearly polarized light that is introduced into the cavity will rotate with frequency of $\omega_{CW}$ for the CW beam, and $\omega_{CCW}$ for the CCW beam). These frequencies given by:

$$\omega_{CW}(\pm B) = (\pm \theta_F + \phi_C) c/L \quad (2)$$

$$\omega_{CCW}(\pm B) = (\pm \theta_F - \phi_C) c/L \quad (3)$$

where L is the round-trip length of the cavity, c is the speed of light, and the dependence on the (lab-frame) angles $\theta_F$ and $\phi_C$ and B field are shown explicitly. The frequencies $\omega_{CW}$ and $\omega_{CCW}$ can be measured by frequency metrology of cavity modes, polarimetry, or by direct measurement of the polarization rotation in the cavity ring down signals described here, and demonstrated recently by Sofikitis et al. "Evanescent-wave and ambient chiral sensing by signal-reversing cavity-ringdown polarimetry" *Nature* 514, 76 (2014), the disclosure of which is incorporated herein by reference.

When a pulsed laser is used or a continuous (cw) laser is used to excite a cavity mode and is turned off quickly, the time-dependent experimental signals $I_{CW}$ and $I_{CCW}$ resemble an exponential decay with polarization oscillation, described by the following equations:

$$I_{CW} = I_0 [e^{-t/\tau_{CW}} \cos^2(\omega_{CW} t + \phi) + \beta] \quad (4)$$

$$I_{CCW} = I_0 [e^{-t/\tau_{CCW}} \cos^2(\omega_{CCW} t + \phi) + \beta] \quad (5)$$

In equations (4-5), $\tau_{CW}$, $\tau_{CCW}$ and $\omega_{CW}$, $\omega_{CCW}$ are the decay times and the polarization beating frequencies, respectively, for the CW and CCW propagation directions, $\beta$ is a parameter to account for experimental imperfections in the light polarization, $\phi$ is a parameter that accounts for error in the determination of the phase of $\omega$ (and is affected by the relative angle between the axes of the input and output polarizers), and $I_0$ is a normalization constant for the signals.

After the signals are analyzed to yield $\omega_{CW}$ and $\omega_{CCW}$ (as a function of the magnetic field polarity), the optical rotation angle $\phi_C$ can then be determined using Eqs (2-3), by performing the following two subtractions:

$$\Delta\omega(\pm B) = |\omega_{CW}(\pm B)| - |\omega_{CCW}(\pm B)| = \pm 2\phi_C(c/L) \quad (6)$$

$$\Delta\omega(+B) - \Delta\omega(-B) = 4\phi_C(c/L) \quad (7)$$

As shown in Eqs. (6-7), the optical rotation angle $\phi_C$ can be determined by subtracting $\omega_{CW}$ and $\omega_{CCW}$, for both positive and negative B fields. These two subtractions allow the measurement of the absolute value of $\phi_C$ without needing to remove the chiral material sample.

For the detection of CD, each output passes through a quarter-wave plate (QWP), followed by a polarizing beam splitter (PBS). The angle between the axis of the QWP and PBS is 45°. Subsequently, as shown in FIG. 12, detector one detects right circularly polarized light, with ring-down time $\tau_R$, and detector two detects right circularly polarized light, with ring-down time $\tau_L$. These ring-down times are given by:

$$\tau_R = \frac{L/c}{1 - R^n + \alpha_R l_0} \text{ and } \tau_L = \frac{L/c}{1 - R^n + \alpha_L l_0},$$

where L is the cavity roundtrip length, R is the reflectivity of each of the n mirrors, $\alpha_R$ and $\alpha_L$ are absorption coefficients of the chiral sample per unit length for right and left circularly polarized light, respectively, and $l_0$ is the length of the chiral sample in one arm of the cavity. The CD signal $\Delta\alpha = \alpha_R - \alpha_L$, is then given by:

$$\Delta\alpha = \frac{L(\tau_R - \tau_L)}{cl_0(\tau_R \tau_L)}$$

The CD signal can be measured for CW, CCW, +B and −B: $\Delta\alpha(CW,+B)$, $\Delta\alpha(CW,-B)$, $\Delta\alpha(CCW,+B)$, and $\Delta\alpha(CCW,-B)$. Finally, the desired CD signal for the chiral sample $\Delta\alpha_c$ is given by the average of pairs of these signals, or of all four of these signals:

$\Delta\alpha_c = [\Delta\alpha(CW,+B) + \Delta\alpha(CW,-B)]/2$, or $\Delta\alpha_c = [\Delta\alpha(CCW,+B) + \Delta\alpha(CCW,-B)]/2$, or $\Delta\alpha_c = [\Delta\alpha(CW,+B) + \Delta\alpha(CW,-B) + \Delta\alpha(CCW,+B) + \Delta\alpha(CCW,-B)]/4$. These averages remove background CD signals that depend on the light propagation direction (CW or CCW), or the magnetic field polarity (+B or −B) such as magnetic circular dichroism.

FIG. 13 similarly provides a corresponding diagram showing a conventional ORD detection method.

While the optical cavity may comprise any appropriate number of reflective elements, such reflective elements comprising, for example, mirrors, reflectors, prisms, or any other components capable of reflecting light, in some implementations disclosed herein, particular advantages may be provided by the use of three, four, five, or any appropriate number of reflective elements within the optical cavity.

Figure 2:
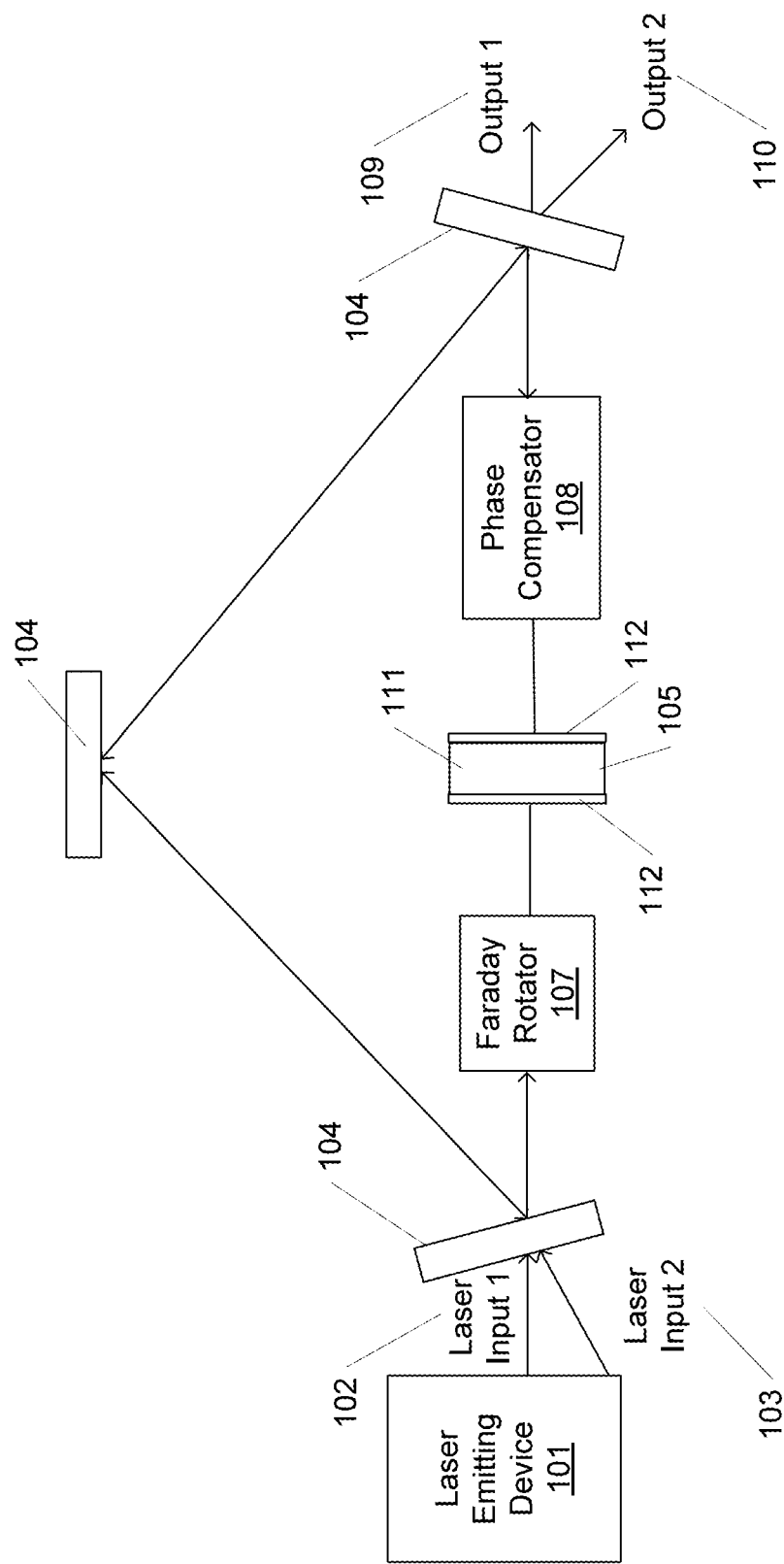
FIG. 2 is a block diagram of an exemplary configuration of a polarimeter comprising three reflective elements which introduces a chiral sample using a flow cell.

FIGS. 1-2 provide exemplary configurations of implementations of the disclosed polarimeter comprising three reflective elements and highlight two ways in which a sample of a chiral material may be introduced into the optical cavity. FIG. 1 depicts an implementation of a polarimeter comprising three reflective elements. One or more laser-emitting devices 101 introduce first 102 and second 103 laser beams into the optical cavity. While any appropriate type of laser emitting device may be used, in some implementations, it is advantageous to utilize a pulse of continuous wave (cw) laser. As shown, this implementation introduces a sample of a chiral material 105 into the cavity by placing the sample 105 in an evanescent wave 106 of a side of a prism 120 at which total internal reflection occurs. The prism is configured such that at least the surfaces of the prism which receive an input of light reflected by one or more reflective elements 104 and provide an output of light from the prism are coated with an anti-reflective coating material that is associated with the specific index of refraction of the chiral material sample 105 which results in total internal reflection of light from the laser beams 102, 103 for at least one side of the prism, at which the chiral material sample 105 is placed in the resultant evanescent wave 106. While FIG. 1 depicts only two reflective elements 104, prism 120 may be considered to comprise the third reflective element due to the manner in which it receives an input and provides an output of light. It should be understood that throughout the remainder of this disclosure, the term "reflective element" may be used to describe a mirror, prism, or any other type of reflective component, however, for clarity in describing some of the embodiments of this disclosure, prisms may be referred to and labeled separately in the figures when it is practical to point out that a specific reflective element in fact, comprises a prism.

FIG. 2 provides an example of an alternative configuration of a cavity enhanced polarimeter comprising three reflective elements 104. As shown, rather than placing the chiral material sample in an evanescent wave of a total internally reflected prism, the chiral material sample may be introduced into the optical cavity using a flow cell 111. While the flow cell 111 may comprise any appropriate shape and dimensions, the flow cell may be substantially cylindrical in shape and comprise an anti-reflective coating 112 on the sides of the flow cell which receive light input and provide light output of the laser light passing through the optical cavity. A sample of the chiral material 105 is located within the flow cell 111 between the anti-reflectively coated input and output sides of the flow cell 111.

Figure 3:
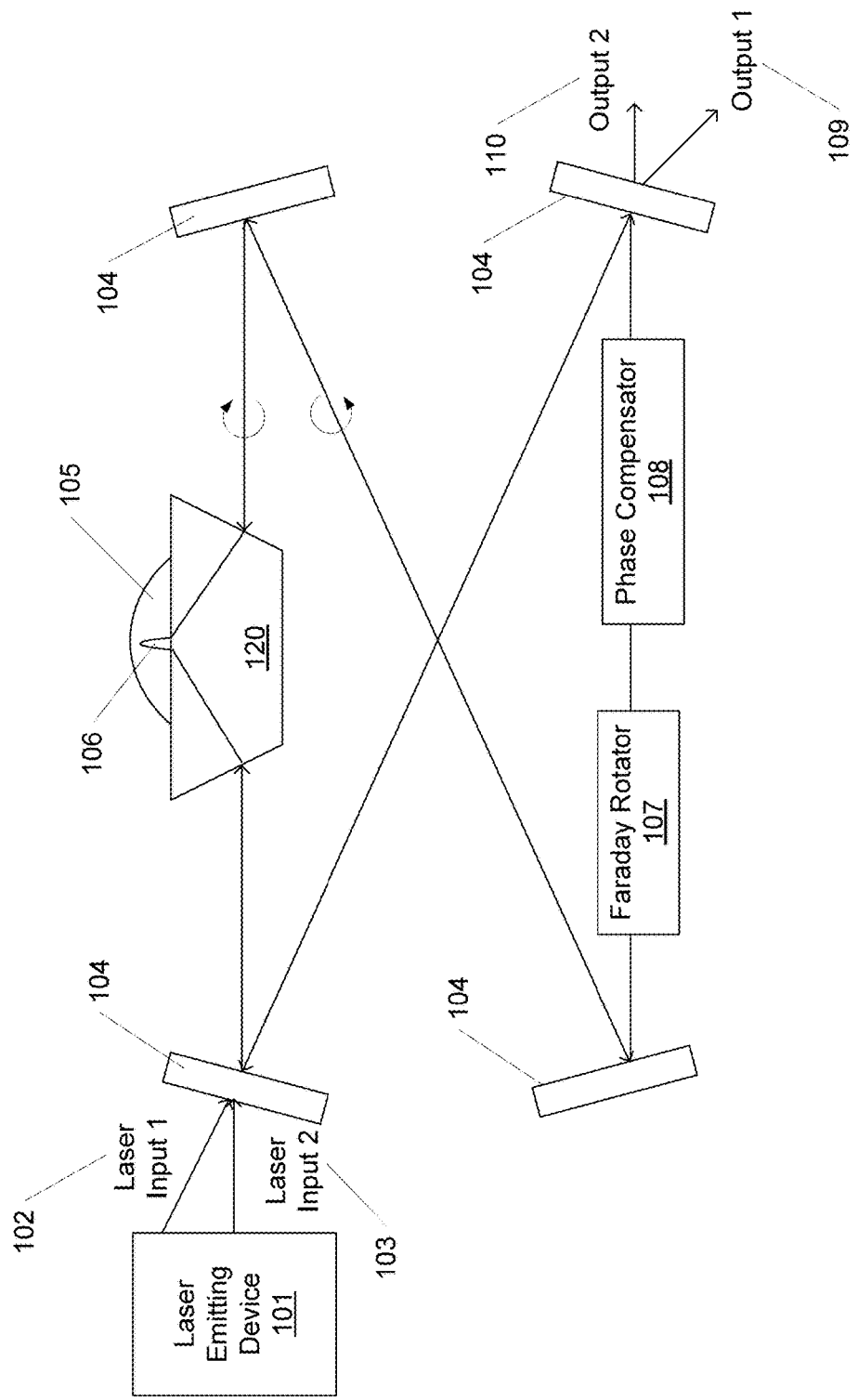
FIG. 3 is a block diagram of an exemplary configuration of a polarimeter comprising four reflective elements in a bowtie configuration which introduces a chiral sample in an evanescent wave of a prism.
Figure 4:
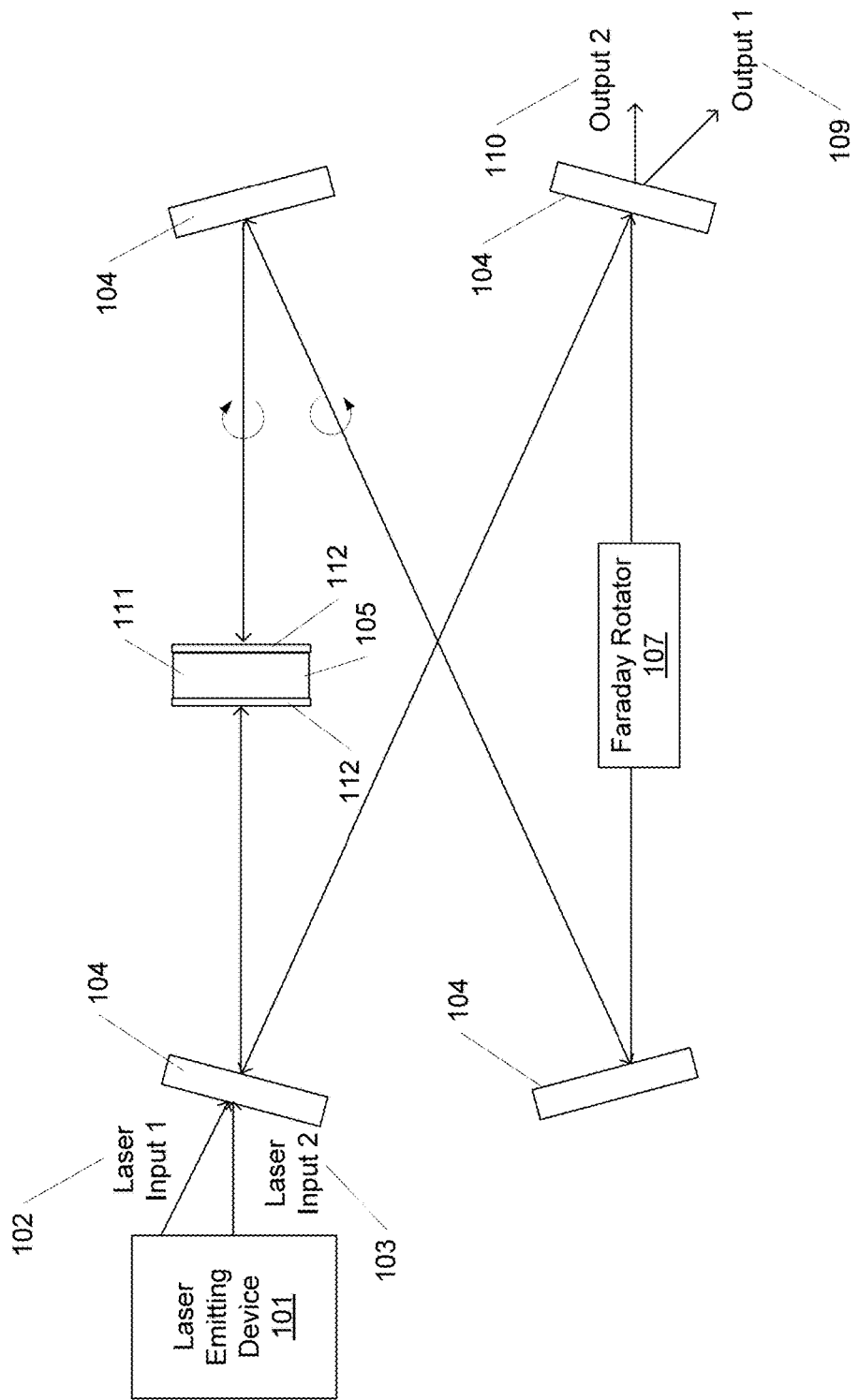
FIG. 4 is a block diagram of an exemplary configuration of a polarimeter comprising four reflective elements in a bowtie configuration which introduces a chiral sample using a flow cell.

FIGS. 3-4 provide exemplary configurations of implementations of a cavity-enhanced polarimeter comprising four reflective elements 104, with FIG. 3 comprising additional an additional reflective element in the form of prism 120. FIG. 2 depicts a chiral sample introduced into the optical cavity in the evanescent wave of a totally internally reflected side of a prism in the manner of FIG. 1 and FIG. 4 utilizes the flow cell for introduction of the chiral material sample in the manner of FIG. 2. Each of these implementations is depicted in a bowtie format for the optical cavity, however, it should be noted that a rectangular ring configuration may also be used instead of a bowtie configuration. Regardless of the number of reflective elements present in the optical cavity, as long as three or more reflective elements are present in the disclosed configurations, light from the first and second laser beams makes many passes through the sample of chiral material, typically in the range of 100 to 10,000, but in some implementations, this range may be as broad as from 100 to 1,000,000 passes without utilizing an intracavity gain medium and as high as 100,000,000 passes when an intracavity gain medium is introduced, which enhances the differences in the polarization oscillation frequencies, $\omega_{CW}$ and $\omega_{CCW}$, detected in output signals 109, 110.

The measurement of ORD and CD requires that linear birefringence in the cavity be minimized as otherwise, it will also be amplified by the cavity, and will suppress the ORD and CD signals. One solution is to make sure that the linear birefringence is naturally small, which can be achieved by ensuring that there is negligible linear birefringence at each optic. For example, if the angle of reflection at each mirror is very small (less than a few degrees), then the linear birefringence can be kept below $10^{-4}$ rad per reflection (and as low as $10^{-6}$ rad). A four-mirror bowtie ring cavity, as shown in FIG. 4, is consistent with these constraints. However, if the linear birefringence is large (e.g. from large incidence angles of a three-mirror cavity, or from birefringence of intracavity optics such as a prism) then a low-loss compensator 108 can be introduced into the cavity, which can be used to tune the linear birefringence $\eta$ to be small, so that the condition $2\theta_F \gg \eta$ can be satisfied. The use of an intra-cavity magneto-optic window such as a Faraday rotator 107 as discussed above also serves to reduce undesirable linear birefringence.

Figure 5:
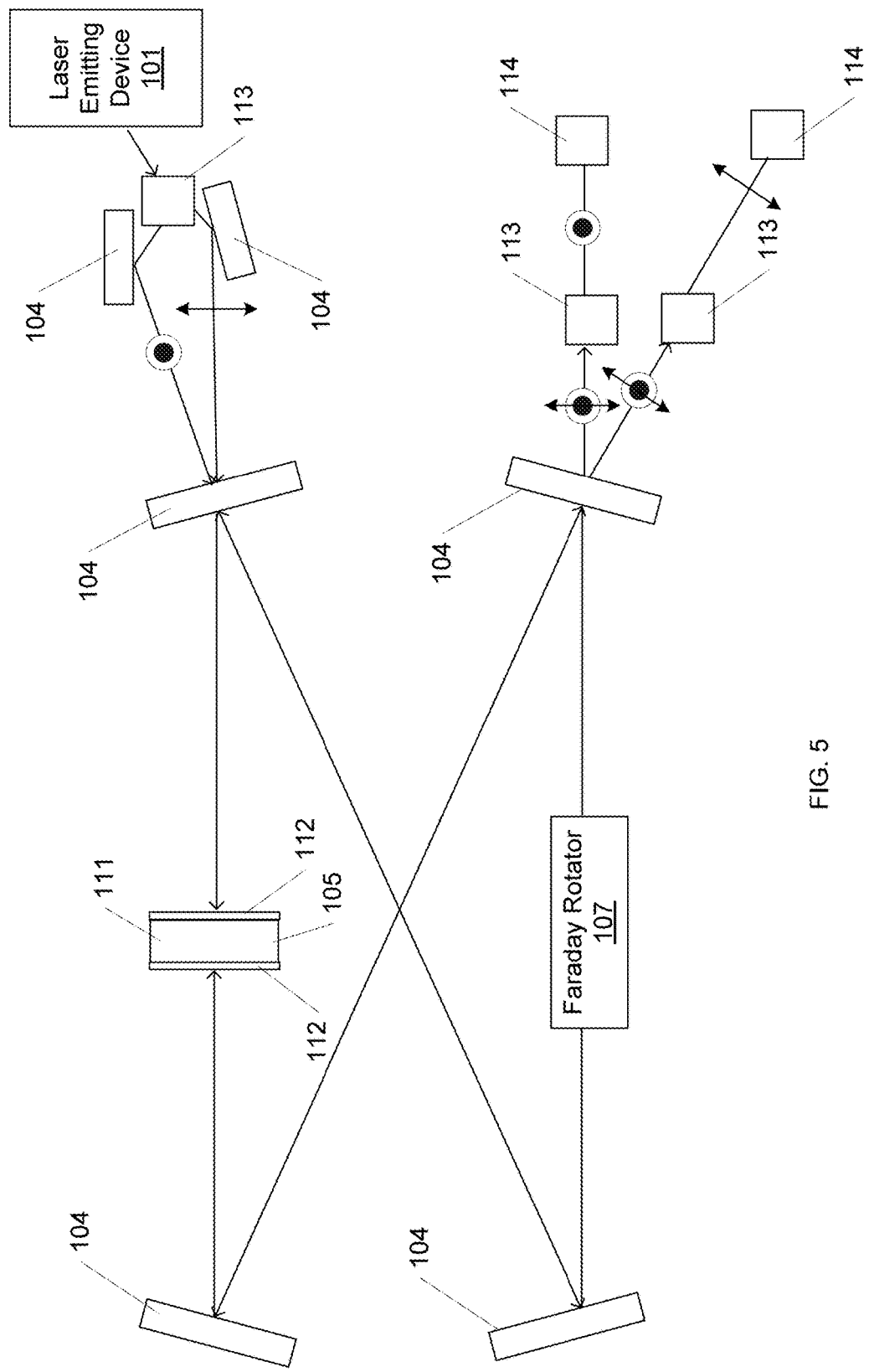
FIG. 5 is a block diagram of an exemplary configuration of a polarimeter comprising polarization beam splitters (PBS) and separate detection devices.

FIG. 5 provides an exemplary configuration of a cavity-enhanced polarimeter that utilizes a single pulsed laser beam (with pulse width shorter than L/c), or a continuous beam that is rapidly turned off or detuned from the cavity resonance (in time shorter than L/c), emitted from the laser emitting device 101 in conjunction with a polarizing beam splitter (PBS) 113 to split the incoming laser beam into CW and CCW beams. The resulting CW and CCW output ring-down signals from the cavity then pass through separate polarizers and reach separate detectors 114 for CD and ORD measurement and analysis.

Figure 6:
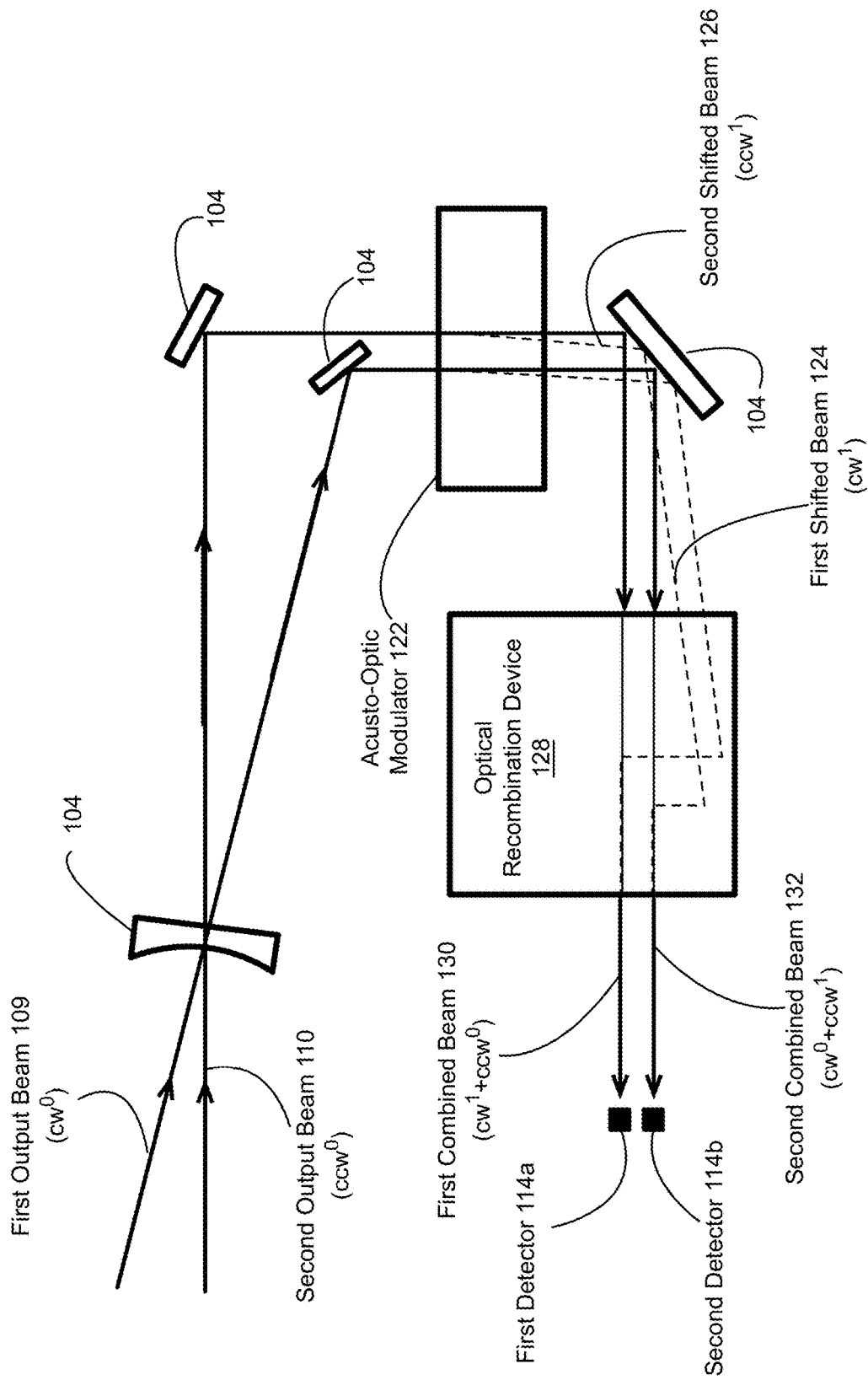
FIG. 6 is a block diagram of an exemplary configuration of part of a polarimeter comprising a continuous beam laser.

FIG. 6 provides an exemplary configuration of part of a cavity-enhanced polarimeter that utilizes a continuous beam laser that is not pulsed. Specifically, FIG. 6 provides an exemplary configuration for performing CD and ORD measurement and analysis on the two ring cavity output signals (e.g. first output laser beam 109, second output laser beam 110) produced by any of the cavities contemplated herein utilizing a laser emitting device 101 that is continuous, such that the output lacks a ring-down signal. As shown, measurement and analysis is performed by recombining the CW (e.g. first output laser beam 109) and CCW (e.g. second output laser beam 110) output beams (with polarization oscillation frequencies $\omega_{CW}^0$ and $\omega_{CCW}^0$, respectively).

Figure 7:
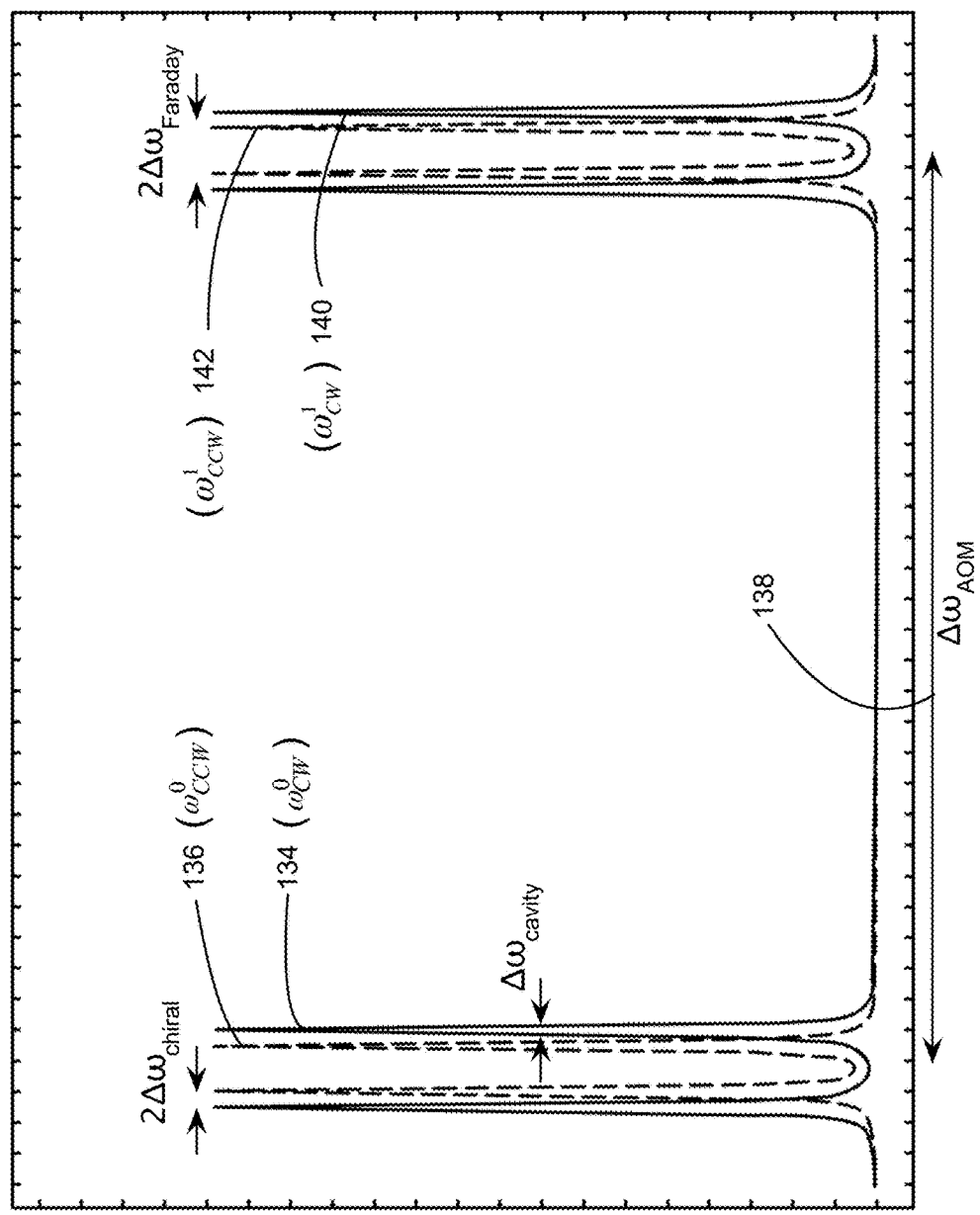
FIG. 7 is an exemplary mode structure of the ring cavity output of FIG. 6.

First, the CW and CCW beams pass through an acousto-optic modulator 122 (AOM), operating at frequency $\omega_{AOM}$ (e.g. offset frequency 138 of FIG. 7), producing beams $cw^1$ (e.g. first shifted beam 124) having a frequency 140 of $\omega_{CW}^1 = \omega_{CW}^0 + \omega_{AOM}$, and $ccw^1$ (second shifted beam 126) having a frequency 142 of $\omega_{CCW}^1 = \omega_{CCW}^0 + \omega_{AOM}$. The mode structure of the cavity output after passing through the AOM 122 is shown in FIG. 7, including the frequencies of the unshifted and shifted beams $cw^0$ (frequency 134), $ccw^0$ (frequency 136), $cw^1$ (frequency 140), and $ccw^1$ (frequency 142).

Subsequently, the beams $cw^1$ (first shifted beam 124) and $ccw^0$ (second output beam 110) are recombined within an optical recombination device 128 forming a first combined beam 130 which is observed at first detector 114a, and produces a beating signal proportional to $\sin(\omega_1 t + \phi_1)$. Similarly, beams $cw^0$ (first output beam 109) and $ccw^1$ (second shifted beam 126) are recombined into a second combined beam 132 which is observed at second detector 114b, and produces a beating signal proportional to $\sin(\omega_2 t + \phi_2)$. Frequencies $\omega_1$ and $\omega_2$ can each be measured with frequency counters, each measuring the signals from detector 1 and detector 2, respectively. Also, the phase difference $(\phi_2-\phi_1)$ between signals $Sin(\omega_1 t+\phi_1)$ and $Sin(\omega_2 t+\phi_2)$ can be measured with a frequency mixer. For a laser linewidth much larger than the cavity linewidth $(\Delta\omega_{laser} \gg \Delta\omega_{cavity})$, the chiral cavity splitting $\Delta\omega_{chiral}$ is given by $\Delta\omega_{chiral}=(\omega_2-\omega_1)/4$. For a laser linewidth much smaller than the cavity linewidth $(\Delta\omega_{laser} \ll \Delta\omega_{cavity})$ the chiral, cavity splitting $\Delta\omega_{chiral}$ is given by: $\Delta\omega_{chiral}=(\phi_2-\phi_1)(c/NL)$, where N is the average number of cavity passes which the light undergoes.

If only one output beam (e.g. first output beam 109) is shifted by the AOM 122 (for experimental convenience), then parts of beams $cw^1$ (first shifted beam 124) and $ccw^0$ (second output beam 110) are recombined and observed at detector 114a, producing a beating signal proportional to $Sin(\omega_1 t+\phi_1)$; similarly parts of beams $cw^0$ (first output beam 109) and $cw^1$ (first shifted beam 124) are recombined and observed at detector 114b, producing a beating signal proportional to $Sin(\omega_2 t+\phi_2)$. As a result, the chiral signals $(\omega_2-\omega_1)$ and $(\phi_2-\phi_1)$ are half the size, as: $\Delta\omega_{chiral}=(\omega_2-\omega_1)/2$, and $\Delta\omega_{chiral}=2(\phi_2-\phi_1)(c/NL)$.

In any of the implementations described herein, measurements of absolute values of CD and ORD may be obtained without the need for removing the chiral material sample and obtaining a null sample as is required according to conventional methodology which relies on background subtraction. This may be accomplished by achieving a reversed chiral signal by inverting the magnetic field in the Faraday rotator, or by inverting the helicity of the input light (for the continuous wave case). This is advantageous because such an absolute measurement of the chiral signal allows measurements in situations in which a null measurement is impossible, such as for thin films on surfaces or open-air measurements, and also allows the cancelling of slow background drifts through rapid signal-reversing background subtractions.

Figure 8A:
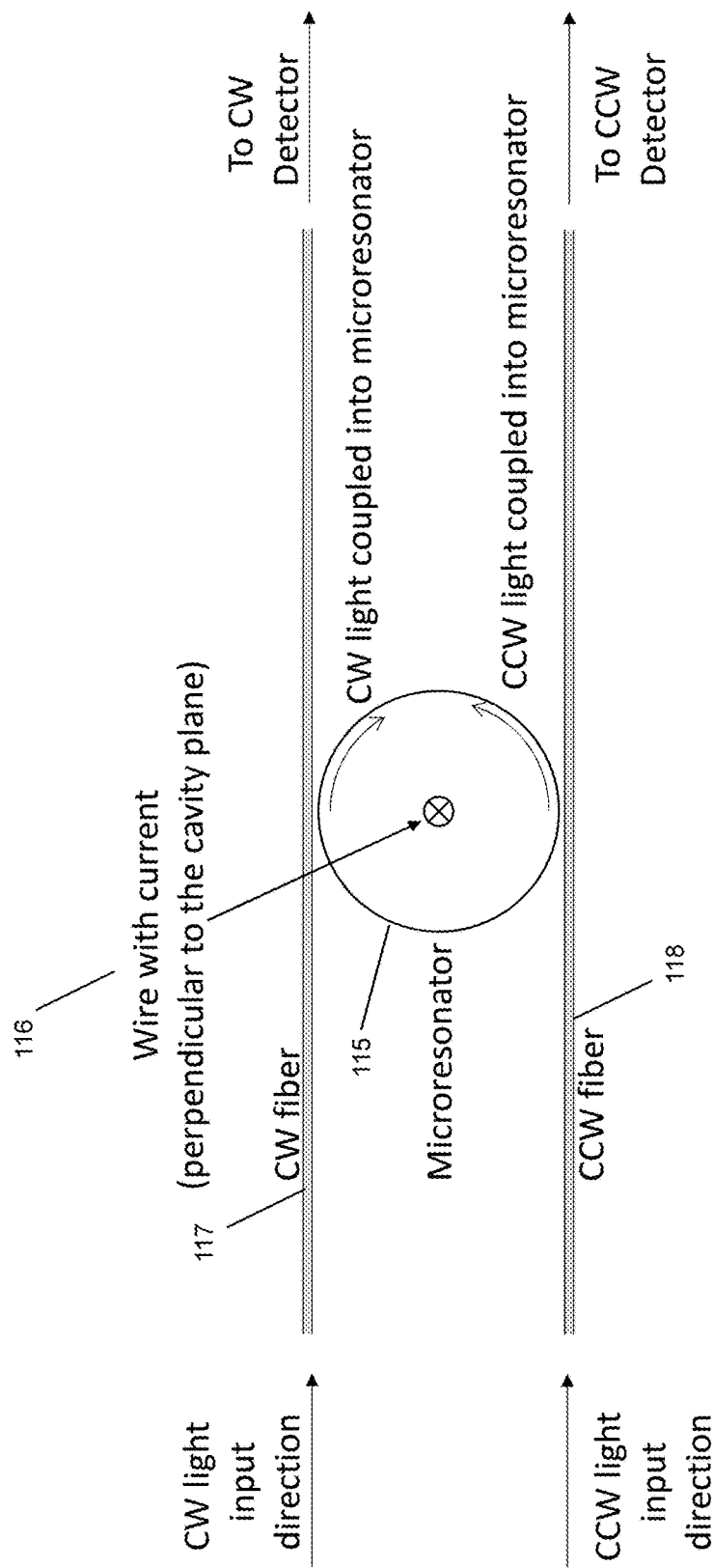
FIGS. 8A-8B provide two embodiments of a top view of a whispering gallery mode microresonator (WGMM).
Figure 8B:
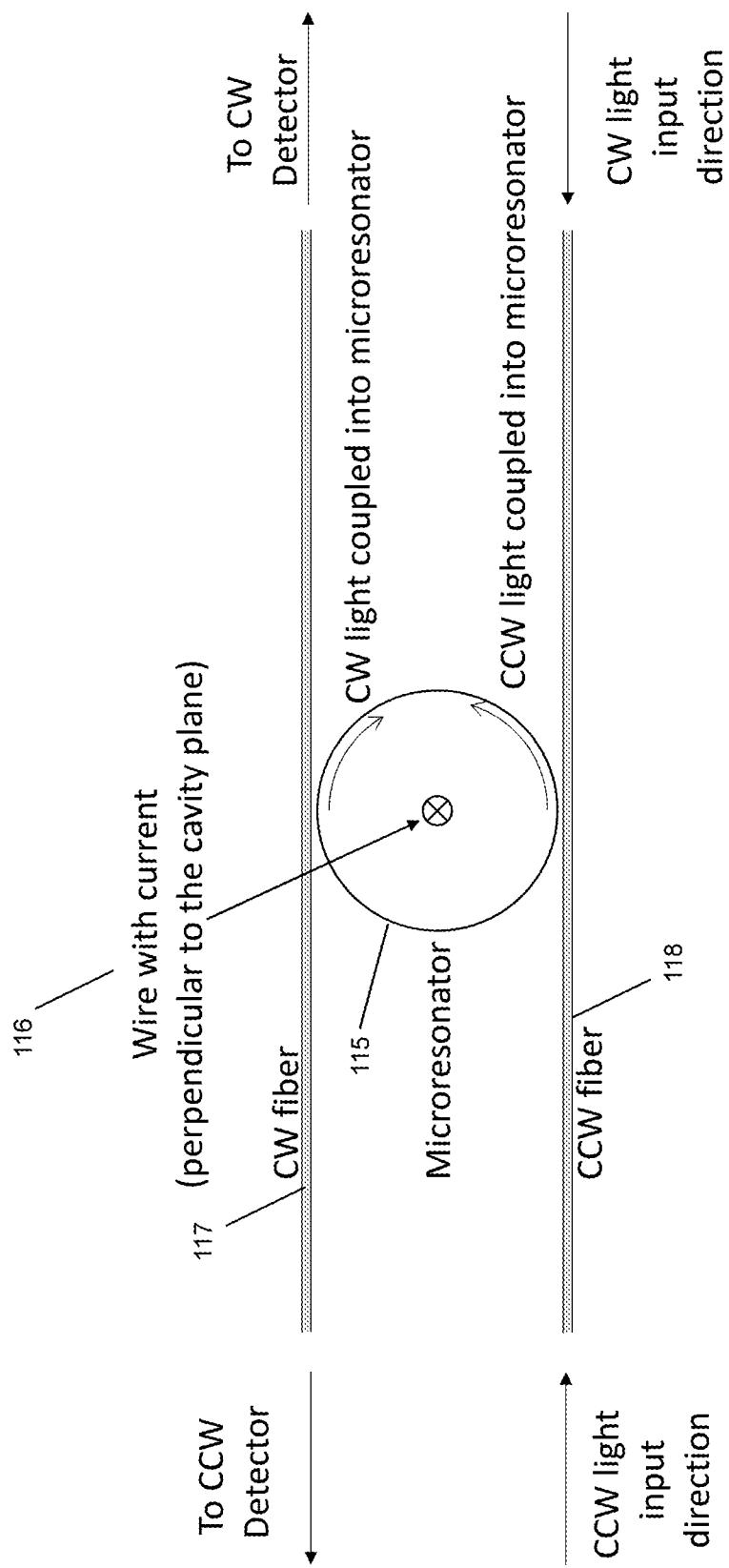
Figure 9:
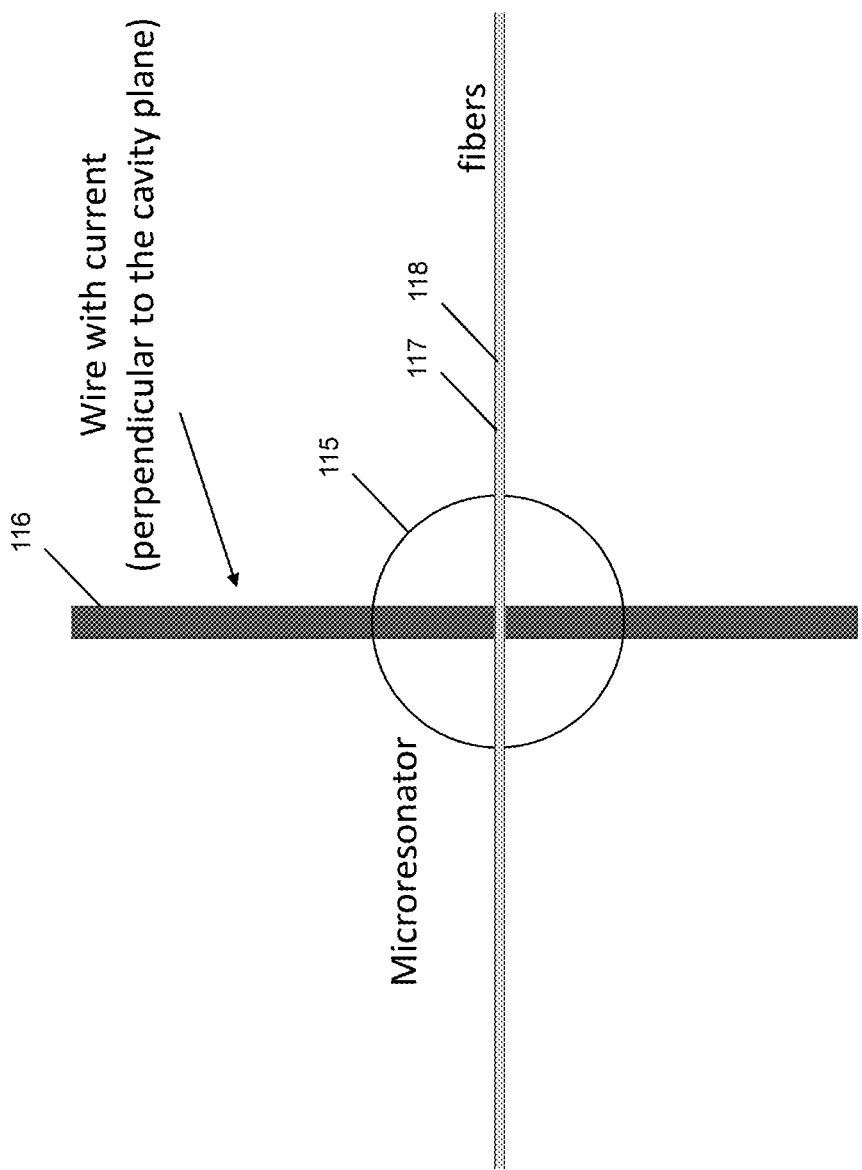
FIG. 9 provides a side view of a whispering gallery mode microresonator (WGMM) of either of the FIG. 8A or 8B.

In some implementations of cavity enhanced polarimeters, one or more whispering gallery mode microresonators (WGMMs) may be used as the Faraday material. WGMMs may be microspheres (typically of radius of 50-500 micrometers), toroidal, or bottle resonators, in which ring cavity propagation is supported, for both CW and CCW directions. WGMMs may be comprised of fused silica, polymethyl methacrylate (PMMA), or materials with high Verdet constants, such as terbium gallium garnet (TGG) or any other appropriate materials. As shown in FIGS. 8A, 8B and 9, a magnetic field along the CW and CCW directions can be applied through a wire 116 that is perpendicular to the cavity plane having an electric current that passes through the center of the microresonator microsphere 115 that produces a magnetic field that is parallel or anti-parallel to the direction of the light propagation. The linear birefringence of the microsphere can be compensated to zero using stress-induced birefringence (as described in W. von Klitzing, R. Long, V. S. Ilchenko, J. Hare, V. Lefevre-Seguin, Optics Letters 26, 166-8 (2001)). CW and CCW cavity modes can be excited through CW and CCW fibers 117, 118 that are brought close to the microsphere 115. FIG. 8A illustrates a side view of a first direction of light input, and FIG. 8B illustrates a side view of a second direction of light input. FIG. 9 illustrates a top view of either FIG. 8A or 8B. While it may appear that fibers 117, 118 are in contact with the microsphere 115, fibers 117, 118 are not in direct contact with microsphere 115, but rather, an evanescent wave couples light between fibers 117, 118 and the microsphere 115. Finally, measurement of ORD and CD at the output of the fibers 117, 118 allow measurement of chirality of samples near the microsphere surface. Chirality is measured as differences in ORD(CW) and ORD(CCW). As WGMMs have already been used to measure the presence of single molecules attached to the WGMMs, using the ORD and CD measurements proposed here may reach the ultimate sensitivity limit of measuring the chirality of single molecules.

Figure 10:
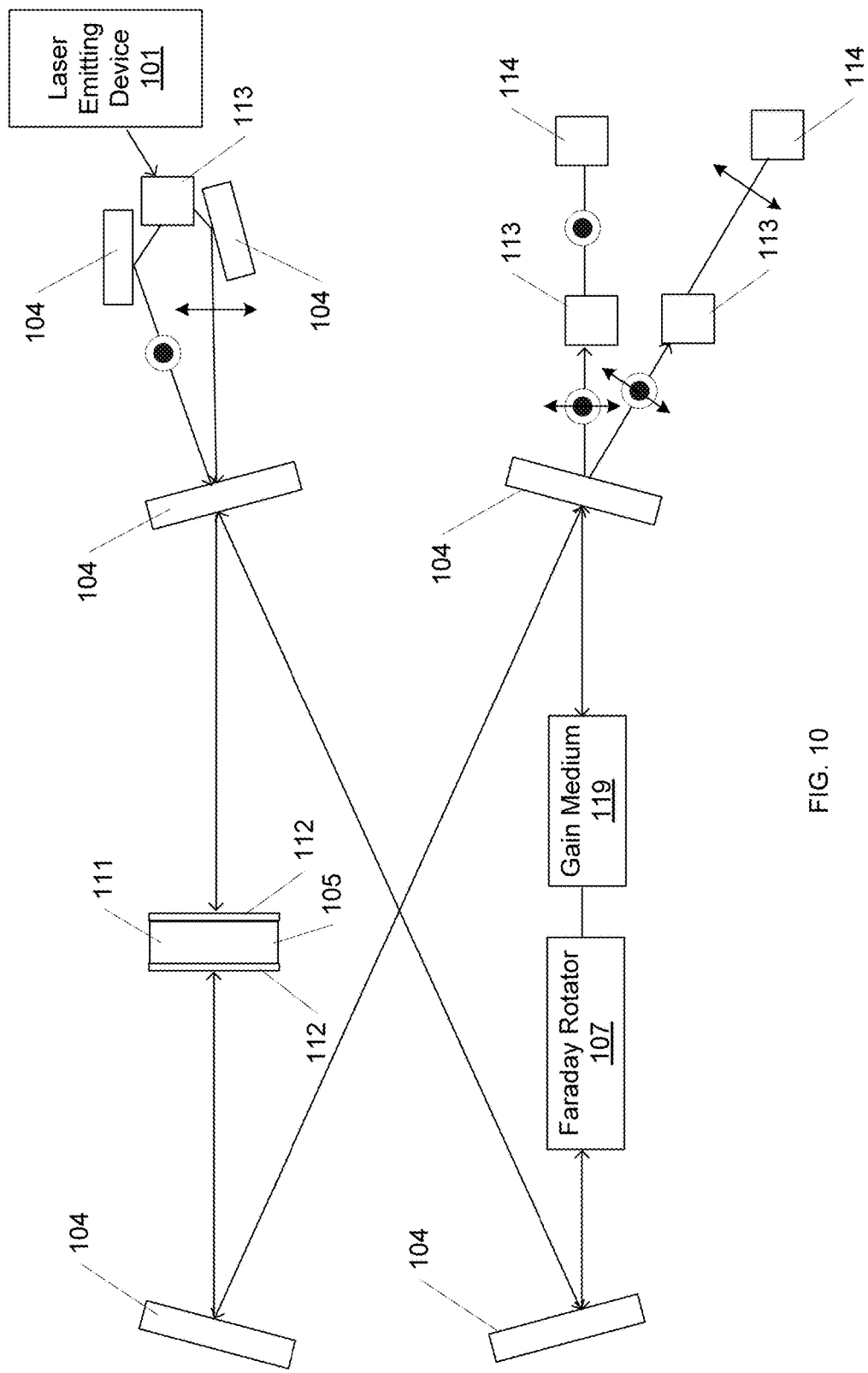
FIG. 10 is a block diagram of an exemplary configuration of a polarimeter comprising an intracavity gain medium.
Figures 11A, 11B:
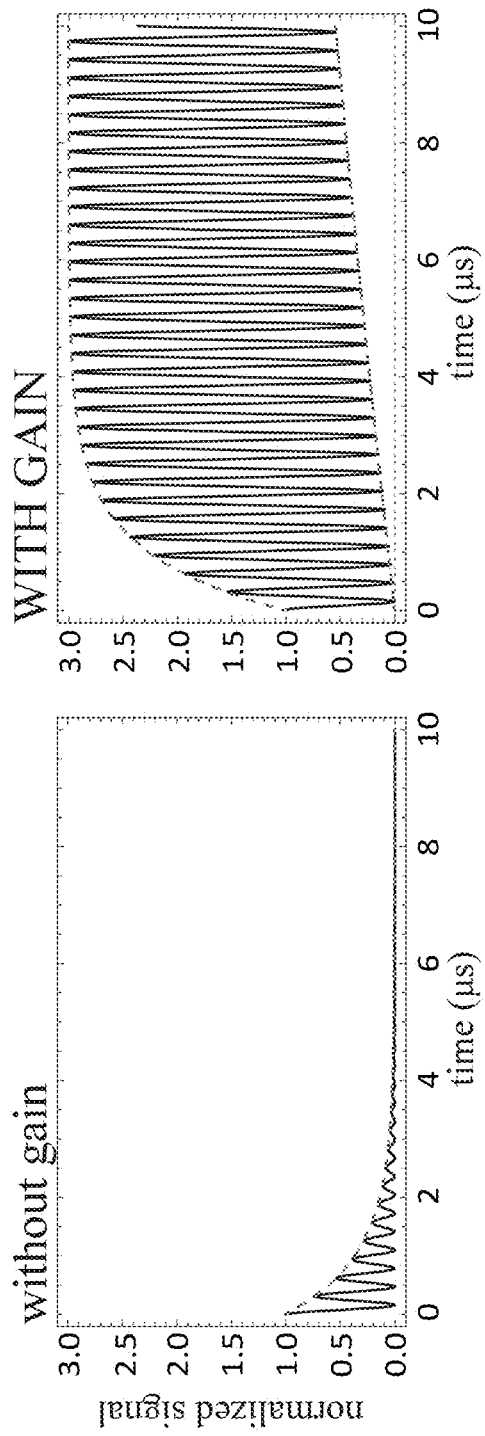
FIGS. 11A-11B provide graphical examples of normalized polarization-oscillation signals without and with the use of an intracavity gain medium, respectively.

As discussed above, the sensitivity enhancement of these cavity-enhanced polarimetry system and methods is given by the average number of cavity passes as limited by the single pass cavity losses. As shown in FIG. 10, to improve this sensitivity even further, an intracavity gain medium 119 may be introduced that amplifies the light independent of the polarization state of the light which may result in few or even no net cavity losses. While the intracavity gain medium 119 is depicted in the particular systematic arrangement of FIG. 10, it is intended that such an intacavity gain medium 119 is applicable in any and all embodiments of cavity enhanced polarimeters described in this disclosure. Using such methods, effective absorption path lengths of 70,000 km may be achieved. Therefore, introducing intracavity gain media 119 to implementations of the cavity-enhanced polarimeters disclosed herein to amplify the chiral signal in a polarization-independent manner may increase the average number of cavity passes to more than $10^7$. Examples of possible intracavity gain media may include, but are not limited to, laser dyes, laser crystals (e.g. titanium sapphire, Nd:YAG), diode lasers, and gaseous gain media (e.g. He—Ne). A graphical depiction of the normalized chiral signal amplitude without the use of intracavity gain medium and with such an intracavity gain medium are provided in FIGS. 11A-11B, respectively.

Through use of a polarimeter configured in accordance with any of the implementations described above, additional surface measurements may be performed that could not previously be made. Such implementation allow for the surface chirality of microscopic samples to be measured, which was not previously possible.

Where the above examples, embodiments and implementations reference examples, it should be understood by those of ordinary skill in the art that other protective gear and manufacturing devices and examples could be intermixed with or substituted for those provided. In places where the description above refers to particular embodiments of protective gear and customization methods, it should be readily apparent that a number of modifications may be made without departing from the spirit thereof and that these embodiments and implementations may be applied to other to protective gear customization technologies as well. Accordingly, the disclosed subject matter is intended to embrace all such alterations, modifications and variations that fall within the spirit and scope of the disclosure and the knowledge of one of ordinary skill in the art.

In places where the description above refers to particular implementations of telecommunication systems and techniques for transmitting data across a telecommunication channel, it should be readily apparent that a number of modifications may be made without departing from the spirit thereof and that these implementations may be applied to other to telecommunication systems and techniques for transmitting data across a telecommunication channel.

The invention claimed is:

1. A polarimeter for measuring chirality of a material comprising:
   an optical ring cavity comprising a plurality of reflective elements configured to promote bi-directional propagation of a laser beam within the cavity;

a laser-emitting device configured to introduce a first input laser beam and a second input laser beam into the ring cavity;

a Faraday rotator and a phase compensator, the Faraday rotator and the phase compensator configured to suppress a birefringent background as the first and second laser beams pass through the ring cavity;

an acousto-optic modulator configured to receive a first output laser beam from the optical ring cavity, shift a frequency of the first output laser beam by an offset frequency, and produce a first shifted laser beam;

an optical recombination device configured to receive the first output laser beam, a second output laser beam from the cavity, and at least the first shifted laser beam to produce a first combined laser beam and a second combined laser beam; and a first detector and a second detector, the first detector configured to receive the first combined laser beam and the second detector configured to receive the second combined laser beam;

wherein the plurality of reflective elements, Faraday rotator, and phase compensator are configured such that light from the first and second input laser beams passes through a chiral material located within the ring cavity a sufficient number of times for a measurement of optical rotary dispersion (ORD) and circular dichroism (CD) of light transmitted through the chiral material and output as the first and second output laser beams to be obtained at the first and second detectors.

2. The polarimeter of claim 1, wherein the first combined laser beam comprises the first shifted beam and the second output beam, and the second combined laser beam comprises the first shifted beam and the first output beam.

3. The polarimeter of claim 1:

wherein the acousto-optic modulator is further configured to receive the second output laser beam from the ring cavity, shift a frequency of the second output laser beam by the offset frequency, and produce a second shifted laser beam;

wherein the optical recombination device is further configured to receive the second shifted laser beam; and wherein the first combined laser beam comprises the first shifted beam and the second output beam, and the second combined laser beam comprises the second shifted beam and the first output beam.

4. The polarimeter of claim 1, further comprising a prism having at least a light input and light output surface comprising an anti-reflective coating such that light from the first and second laser beams is totally internally reflected for at least one surface of the prism at which the chiral material is located within an evanescent wave at the at least one surface of the prism.

5. The polarimeter of claim 1, further comprising a flow cell within which the chiral material is located wherein the flow cell comprises one or more anti-reflective coated windows.

6. The polarimeter of claim 1, wherein the light from the first and second laser beams passes through the chiral material is in a range of 100 to 10,000 times.

7. The polarimeter of claim 1, wherein a magnetic field of the Faraday rotator is reversed such that the ORD dispersion is reversed, so that an absolute measurement of ORD of light passing through the chiral material is obtainable without requiring a null sample.

8. The polarimeter of claim 1, wherein the Faraday rotator comprises a whispering gallery mode microresonator (WGMM) configured to pass an electric current therethrough to produce a Faraday Effect, such that a measurement of ORD and CD is obtained when the chiral material is located at a surface of the WGMM.

9. The polarimeter of claim 1, wherein the laser-emitting device is configured to emit a continuous wave laser beam.

10. The polarimeter of claim 1, wherein the plurality of reflective elements comprises four reflective elements and the optical ring cavity comprises a bowtie ring cavity.

11. A method of measuring chirality of a material comprising:

promoting bi-directional propagation of a laser beam within an optical ring cavity of a polarimeter comprised of a plurality of reflective elements;

introducing a first input laser beam and a second input laser beam into the ring cavity using a laser emitting device;

suppressing a birefringent background as the first and second input laser beams pass through the ring cavity using a Faraday rotator and a phase compensator;

receiving a first output laser beam produced by the ring cavity at an acousto-optic modulator;

shifting a frequency of the first output laser beam by an offset frequency using the acousto-optic modulator to produce a first shifted laser beam;

combining the first output laser beam, a second output laser beam produced by the ring cavity, and at least the first shifted laser beam into a first combined laser beam and a second combined laser beam using an optical recombination device; and measuring the first combined beam using a first detector and the second combined beam using a second detector;

wherein the plurality of reflective elements, Faraday rotator, and phase compensator are configured such that light from the first and second input laser beams passes through a chiral material located within the ring cavity a sufficient number of times for a measurement of optical rotary dispersion (ORD) and circular dichroism (CD) of light transmitted through the chiral material and output as the first and second output laser beams to be obtained at the first and second detectors.

12. The method of claim 11, wherein the first combined laser beam comprises the first shifted beam and the second output beam, and the second combined laser beam comprises the first shifted beam and the first output beam.

13. The method of claim 11, further comprising:

receiving the second output laser beam at the acousto-optic modulator; and shifting a frequency of the second output laser beam by the offset frequency using the acousto-optic modulator to produce a second shifted laser beam;

wherein the second shifted beam is combined with the first and second output beams and the first shifted beam using the optical recombination device to produce the first and second combined beams; and wherein the first combined laser beam comprises the first shifted beam and the second output beam, and the second combined laser beam comprises the second shifted beam and the first output beam.

14. The method of claim 11, further comprising totally internally reflecting light from the first and second laser beams for at least one surface of a prism having at least a light input and light output surface comprising an anti-reflective coating, the chiral material being located within an evanescent wave at the at least one surface of the prism for which the light is totally internally reflected.

15. The method of claim 11, wherein the polarimeter further comprises a flow cell within which the chiral material is located, wherein the flow cell comprises comprising one or more anti-reflective coated windows within which the chiral material is located.

16. The method of claim 11, wherein the light from the first and second laser beams passes through the chiral material is in a range of 100 to 10,000 times.

17. The method of claim 11, further comprising obtaining an absolute measurement of ORD of light passing through the chiral material without requiring a null sample by reversing a magnetic field of the Faraday rotator.

18. The method of claim 11, further comprising increasing a number of times the light from the first and second input laser beams passes through the chiral material using an intracavity gain medium within the cavity, wherein the intracavity gain medium amplifies the light independent of a polarization state of the light.

19. The method of claim 11, wherein the laser-emitting device emits a continuous wave laser beam.

20. The method of claim 11, wherein the plurality of reflective elements comprises four reflective elements and the optical ring cavity comprises a bowtie ring cavity.

* * * * *